(12) United States Patent
Treybig et al.

(10) Patent No.: US 7,053,127 B1
(45) Date of Patent: May 30, 2006

(54) QUATERNIZED AMIDO CYCLIC AMINE SURFACTANT

(75) Inventors: Duane S Treybig, Sugar Land, TX (US); Kin-Tai Chang, Sugar Land, TX (US)

(73) Assignee: Nalco Company, Naperville, IL (US)

( * ) Notice: Subject to any disclaimer, the term of this patent is extended or adjusted under 35 U.S.C. 154(b) by 316 days.

(21) Appl. No.: 10/244,651

(22) Filed: Sep. 16, 2002

(51) Int. Cl.
*B01F 17/22* (2006.01)
*C07C 233/89* (2006.01)
*C07C 235/86* (2006.01)
*C07C 237/50* (2006.01)

(52) U.S. Cl. .......................... 516/203; 516/59; 516/60; 516/67; 516/68; 516/69; 516/102; 516/128; 516/130; 516/149; 516/150; 516/151; 516/169; 516/201; 554/51; 554/52; 554/106; 554/124; 554/150; 554/161; 554/163

(58) Field of Classification Search ................ 554/51, 554/52, 106, 124, 150, 161, 163; 516/59, 516/60, 67, 68, 69, 102, 128, 130, 149, 150, 516/151, 169, 201, 203
See application file for complete search history.

(56) References Cited

U.S. PATENT DOCUMENTS

| | | | | |
|---|---|---|---|---|
| 2,252,863 A | * | 8/1941 | Raymond et al. ........... 552/554 |
| 3,869,483 A | * | 3/1975 | Mod et al. .................... 554/52 |
| 4,303,588 A | * | 12/1981 | Okabe et al. ................. 554/51 |
| 5,182,033 A | * | 1/1993 | Lagerman .................... 510/519 |
| 5,563,214 A | * | 10/1996 | Share et al. ................. 524/809 |
| 5,977,183 A | * | 11/1999 | Scepanski .................... 514/643 |
| 6,258,859 B1 | | 7/2001 | Dahayanake et al. |
| 2002/0002170 A1 | * | 1/2002 | Luond et al. .......... 514/253.02 |

FOREIGN PATENT DOCUMENTS

JP 2003107715 A * 4/2003
WO WO 01/18147 3/2001

OTHER PUBLICATIONS

Mod et al. (Journal of Medicinal Chemistry, 1971, vol. 14, No. 6, p. 558-9).*
Kiuchi et al. (Chem. Pharm. Bull. 40(12) 3234-3244, 1992).*
English Translation of JP 07-233033 obtained from the JPO Web-site, Sep. 1995, Kawai.*

* cited by examiner

*Primary Examiner*—Jeffrey B. Robertson
(74) *Attorney, Agent, or Firm*—Michael B. Martin; Thomas M. Breininger

(57) ABSTRACT

A quaternary surfactant comprising a cyclic diamine group, compositions comprising the quaternized amido cyclic amine surfactant, a gelled aqueous composition comprising the quaternized amido cyclic amine surfactant, use of the gelled aqueous well treatment applications and methods of preparation and intermediates used to prepare the quaternized amido cyclic amine surfactant.

22 Claims, No Drawings

QUATERNIZED AMIDO CYCLIC AMINE SURFACTANT

TECHNICAL FIELD

This invention is a quaternized amido cyclic amine surfactant, compositions comprising the quaternized amido cyclic amine surfactant, a gelled aqueous composition comprising the quaternized amido cyclic amine surfactant, use of the gelled aqueous well treatment applications and methods of preparation and intermediates used to prepare the quaternized amido cyclic amine surfactant.

BACKGROUND OF THE INVENTION

Alkyl amido alkylene quaternary salt viscoelastic surfactants and their use as viscosifiers for aqueous solutions used in oil field applications are disclosed in International Application Publication Number WO 01/18147.

Alkyl amido alkylene and alkenyl amido alkylene viscoelastic surfactant molecules containing carboxyalkyl groups, and their use as viscosifiers for aqueous solutions used in oil field applications are disclosed in U.S. Pat. No. 6,258,859.

Neither of the foregoing references discloses quaternized surfactant compositions comprising a cyclic diamine group.

SUMMARY OF THE INVENTION

This invention is a quaternized amido cyclic amine surfactant of formula

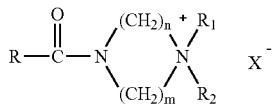

wherein R is selected from the group consisting of $C_{12}$–$C_{30}$ alkyl, $C_{12}$–$C_{30}$ alkenyl, $C_{12}$–$C_{30}$ arylalkyl and $C_{12}$–$C_{30}$ cycloalkylalkyl; $R_1$ and $R_2$ are independently selected from $C_3$–$C_8$ cycloalkyl, aryl, $C_6$–$C_{10}$ arylalkyl, $C_2$–$C_5$ hydroxyalkyl and $C_1$–$C_5$ alkyl; m and n are independently integers of 1 to about 4; and X is absent or is selected from halide and methyl sulfate, provided that when X is absent, one of $R_1$ and $R_2$ is substituted with carboxylate or sulfonate.

Thickened aqueous compositions comprising the quaternized amido cyclic amine surfactant of this invention typically require less surfactant in their formulation than the those prepared using the amido alkyl quaternary surfactant described in WO 01/18147 or prepared using other commercially available surfactants. Since water, alcohol solvents and inorgnic salt is usually cheaper than the surfactant, less unsaturated amido alkylpiperazine quaternary surfactant reduces the overall cost of the formulation.

DETAILED DESCRIPTION OF THE INVENTION

Definitions of Terms

"Alcohol" means a straight or branched aliphatic hydrocarbon substituted by one hydroxy group. Representative alcohols include methanol, ethanol, propanol, isopropanol, butanol, 2-ethylhexanol, hexanol, octanol, decanol, and the like.

"Alkenyl" means a monovalent group derived from a straight or branched hydrocarbon containing at least one carbon—carbon double bond by the removal of a single hydrogen atom.

"Alkoxy" means a $C_1$–$C_4$ alkyl group attached to the parent molecular moiety through an oxygen atom. Representative alkoxy groups include methoxy, ethoxy, propoxy, butoxy, and the like. Methoxy and ethoxy are preferred.

"Alkyl" means a monovalent group derived from a straight or branched chain saturated hydrocarbon by the removal of a single hydrogen atom. Representative alkyl groups include methyl, ethyl, n- and iso-propyl, n-, sec-, iso- and tert-butyl, and the like.

"Alkylene" means a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

"Alkylene oxide" means an aliphatic $C_2$ to $C_4$ epoxide, for example ethylene oxide, propylene oxide and butylene oxide.

"Aryl" means substituted and unsubstituted aromatic carbocyclic radicals and substituted and unsubstituted heterocyclic having from 5 to about 14 ring atoms. Representative aryl include phenyl naphthyl, phenanthryl, anthracyl, pyridyl, furyl, pyrrolyl, quinolyl, thienyl, thiazolyl, pyrimidyl, indolyl, and the like. The aryl is optionally substituted with one or more groups selected from hydroxy, halogen, $C_1$–$C_4$ alkyl and $C_1$–$C_4$ alkoxy.

"Arylalkyl" means an aryl group attached to the parent molecular moiety through an alkylene group. $C_{12}$–$C_{30}$ arylalkyl means an arylalkyl group where the number of carbon atoms in the aryl group and the alkylene group is selected such that there is a total of about 12 to about 30 carbon atoms in the arylalkyl group. $C_6$–$C_{18}$ arylalkyl means an arylalkyl group where the number of carbon atoms in the aryl group and the alkylene group is selected such that there is a total of about 6 to about 18 carbon atoms in the arylalkyl group.

"Carboxylate" means —$CO_2^-$.

"Cycloalkyl" means a monovalent group derived from a monocyclic or bicyclic saturated carbocyclic or heterocyclic ring compound by the removal of a single hydrogen atom. Representative cycloalkyl include cyclopropyl, cyclobutyl, cyclopentyl, cyclohexyl, bicyclo[2.2.1]heptanyl, piperazinyl, bicyclo[2.2.2]octanyl, homopiperazinyl, imidazolidinyl, and the like.

"Cycloalkylalkyl" means a cycloalkyl group attached to the parent molecular moiety through an alkylene group. The number of carbon atoms in the alkylene group is selected such that there is a total of about 12 to about 30 carbon atoms in the cycloalkylalkyl group.

"Diol" means a straight or branched aliphatic hydrocarbon substituted by two hydroxy groups. Representative diols include ethylene glycol, 1,2-propylene glycol, butylene glycol, 2-methyl-2,4-pentanediol, hexylene glycol, and the like.

"Halo" and "halogen" mean chlorine, fluorine, bromine and iodine.

"Hydroxyalkyl" means an alkyl group as defined herein substituted by one to three hydroxyl groups with the proviso that no more than one hydroxy group may be attached to a single carbon atom of the alkyl group. Representative hydroxyalkyl include hydroxyethyl, 2-hydroxypropyl, and the like.

"Salt" means the alkali or alkaline earth metal or ammonium salt of an inorganic or organic anionic counterion. Representative alkali or alkaline earth metals include sodium, lithium, potassium, calcium, magnesium, and the like. Representative anionic counterions include chloride, bromide, iodide, salicylate, toluenesulfonate, 3-hydroxy-2-naphthalenecarboxylate, cumene sulphonate, p- and m-chlorobenzoates, t-butyl and ethyl phenate, 2,5-dichlorophenate, 2,4,5-trichlorophenate, 2,3,5,6-tetrachlorophenate, p-methylphenate, m-chlorophenate, 3,5,6-trichloropicolinate, 4-amino-3,5,6-trichloropicolinate, 2,4-dichlorophenoxyacetate and the like.

"Sulfonate" means $-SO_3^-$.

PREFERRED EMBODIMENTS

The preparation of the quaternized amido cyclic amine surfactant of this invention is outlined in Scheme 1, where R, $R_1$, $R_2$, n, m and X are as defined herein.

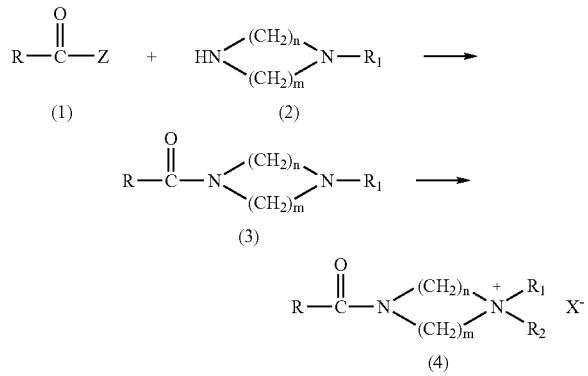

As shown in Scheme 1, reaction of cyclic diamine (2) with a fatty carboxylic acid, ester, acid choride of formula $R_1C(O)Z$, where Z is halide, OH or alkoxy provides the tertiary amide (3).

Preferably, the cyclic diamine is reacted with about 1.0 to about 1.1 molar equivalents of the fatty carboxylic acid, ester or acid choride at a temperature of about 60° C. to about 180° C. for about 1 to about 30 hours. In cases where Z is alkoxy, the reaction is preferably conducted in the presence of a base such as sodium methoxide. Where Z is hydroxy, the reaction is preferably done in the absence of solvent.

Representative cyclic diamines (2) include 1-methylpiperazine, 1-ethylpiperazine, 1-(2-hydroxyethyl)piperazine, 1-(2-hydroxypropylpiperazine), 1-benzylpiperazine, 1-methylimidazolidine, 1-methyl-homopiperazine (hexahydro-1-methyl-1H-1,4-diazepine), 1-ethyl-homopiperazine and the like and mixtures thereof.

The carboxylic acids, esters or acid chlorides may be saturated and unsaturated and contain between 12 to 30 carbons exclusive of the alkoxy group of the ester. Alkyl and alkenyl groups may be straight chain or branched.

Representative unsaturated carboxylic acids $RCO_2H$ include 6-octadecenoic acid (oleic acid, $C_{18}$); 9,11,13-octadecatrienoic acid ($C_8$); 12-hydroxy-9-octadecenoic acid ($C_{18}$); 5,8,11,14-eicosatetraenoic acid ($C_{20}$); eicosenoic acid ($C_{20}$); heneicosenoic acid ($C_{21}$); 13-docosenoic acid (erucic acid, $C_{22}$); tetracosenoic acid ($C_{24}$); pentacosenoic acid ($C_{25}$), heptacosenoic acid ($C_{27}$); and the like and mixtures thereof.

Representative saturated carboxylic acids $RCO_2H$ include eicosanoic acid ($C_{20}$); heneicosanoic acid ($C_2$); docosanoic acid (behenic acid, $C_{22}$); tricosanoic acid ($C_{23}$); tetracosanoic acid ($C_{24}$); pentacosanoic acid ($C_{25}$); heptacosanoic acid ($C_{27}$); and the like and mixtures thereof.

Representative branched unsaturated and saturated acids $RCO_2H$ include 3-methylhexadecanoic acid; 7-methylhexadecanoic acid; 13-methylhexadecanoic acid; 14-methyl-11-eicosenoic acid; 2-hydroxy-18-oxa-19-methyl-4-eicosenoic acid; and the like and mixtures thereof.

Representative alkyl esters of saturated and unsaturated acids $RCO_2R'$ include 2-methylhexadecanoic acid methyl ester; 8-ethyl-9-methylhexadecanoic acid methyl ester; 18-methyl-15-eicosenoic acid methyl ester; 14-methyl-11-eicosenoic acid methyl ester; 9,12,15-octadecatrienoic acid methyl ester; docosanoic acid methyl ester; and the like and mixtures thereof.

Acid chlorides of saturated and unsaturated acids RCOCl include include oleoyl chloride, octadecanoyl chloride, docosanoyl chloride, eicosanoyl chloride, 9-tetracosenoyl chloride, 15-tetracosenoyl chloride, and the like and mixtures thereof.

In cases where X is halide, the tertiary amide (3) is dissolved in a $C_1$–$C_4$ alcohol and quaternized with about 1 to about 1.5 molar equivalents of a $C_1$–$C_5$ alkyl halide, preferably about 1.1 to about 1.3 molar equivalents of methyl chloride, at a temperature of about 30° C. to about 100° C. for about 6 to about 27 hours to form the quaternized amido cyclic amine surfactant (4).

When X is methyl sulfate, the tertiary amide (3) is dissolved in a suitable solvent, such as an $C_1$–$C_4$ alcohol or diol and quaternized with about 1 to about 1.5 molar equivalents of a dimethyl sulfate, preferably about 1.0 to about 1.1 molar equivalents of dimethyl sulfate at reflux temperature to form the quaternized amido cyclic amine surfactant.

Isopropanol and methanol are the preferred solvents for the quaternization as they exhibit the best ability at solubilizing the quaternary salt by breaking the gel phase formed. Isopropanol is preferred over methanol because of the toxicity issues associated with use of methanol.

In cases where X is absent, one of the groups $R_1$ and $R_2$ is substituted with a carboxylate or sulfonate.

Accordingly, in another aspect, this invention is a method of preparing a cyclic diamine of formula

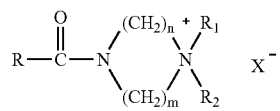

wherein R is selected from the group consisting of $C_{12}$–$C_{30}$ alkyl, $C_{12}$–$C_{30}$ alkenyl, $C_{12}$–$C_{30}$ arylalkyl and $C_{12}$–$C_{30}$ cycloalkylalkyl; $R_1$ and $R_2$ are independently selected from $C_3$–$C_8$ cycloalkyl, aryl, $C_6$–$C_{10}$ arylalkyl, $C_2$–$C_5$ hydroxyalkyl and $C_1$–$C_5$ alkyl; m and n are independently integers of 1 to about 4; and X is selected from halide and methyl sulfate, comprising reacting a tertiary amide of formula

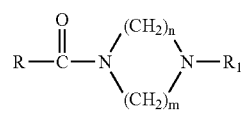

with methyl halide or dimethyl sulfate.

Quaternized amido cyclic amine surfactants (4) substituted with a sulfonate group are prepared by reacting the tertiary amide of formula

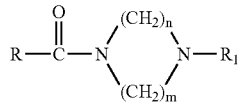

with a halo-substituted $C_3$–$C_8$ cycloalkyl-, aryl-, $C_6$–$C_{10}$ arylalkyl-, $C_2$–$C_5$ hydroxyalkyl- or $C_1$–$C_5$ alkylsulfonate or by ring opening of a sultone.

For example, the propane sulfonate betaine can be prepared by reacting the tertiary amide with about 1 to about 1.5, preferably about 1.0 to about 1.1 molar equivalents of 1,3-propane sultone in water or any other suitable solvent at a temperature of about 25° C. to 95° C. for 10 minutes to 8 hours.

The butane sulfonate betaine can be prepared by reacting the tertiary amide with about 1 to about 1.6 molar equivalents of 1,4-butane sultone either neat or in a suitable solvent such as ethylene dichloride. When the reaction is carried out neat it is generally carried out at 120° C. to 250° C., preferably 160° C. to 190° C. with a catalyst. When the reaction is carried out with a solvent, the contents are heated at reflux.

A hydroxy-substituted propane sulfonate betaine can be prepared by reacting the tertiary amine with about 1 to about 1.8 molar equivalents of the sodium salt of 3-chloro-2-hydroxy-1-propanesulfonic acid in a suitable solvent at reflux temperature. Representative solvents include water, alcohols, diols and their blends. A catalyst such as sodium hydroxide can be used to enhance the reaction. See U.S. Pat. No. 4,853,138.

Quaternized amido cyclic amine surfactants (4) substituted with a carboxlate group are prepared by reacting the tertiary amide of formula

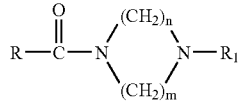

with a halo-substituted $C_3$–$C_8$ cycloalkyl-, aryl-, $C_6$–$C_{10}$ arylalkyl-, $C_2$–$C_5$ hydroxyalkyl- or $C_1$–$C_5$ alkyl carboxylic acid or ester such as sodium chloroacetate or chloroacetic acid neutralized with sodium hydroxide.

For example, the tertiary amide is dissolved in a suitable solvent, such as glycerine, an alcohol or a glycol and reacted with about 0.9 to about 1.5, preferably about 0.9 to about 1.1 molar equivalents of sodium chloroacetate at a temperature of about 60° C. to about 120° C., preferably less than about 100° C., for about 2 to about 10 hours, preferably for 3 to 5 hours to form the quaternized amido cyclic amine surfactant.

Accordingly, in another aspect, this invention is a method of preparing a quaternized cyclic diamine of formula

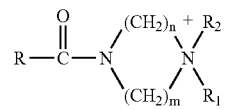

wherein R is selected from the group consisting of $C_{12}$–$C_{30}$ alkyl, $C_{12}$–$C_{30}$ alkenyl, $C_{12}$–$C_{30}$ arylalkyl and $C_{12}$–$C_{30}$ cycloalkylalkyl; $R_1$ is selected from $C_3$–$C_8$ cycloalkyl, $C_5$–$C_{14}$ aryl, $C_6$–$C_{10}$ arylalkyl, $C_2$–$C_5$ hydroxyalkyl and $C_1$–$C_5$ alkyl; $R_2$ is selected from $C_3$–$C_8$ cycloalkyl, aryl, $C_6$–$C_{10}$ arylalkyl, $C_2$–$C_5$ hydroxyalkyl and $C_1$–$C_5$ alkyl wherein the cycloalkyl, aryl, arylalkyl, hydroxyalkyl or alkyl is substituted with carboxylate or sulfonate; and m and n are independently integers of 1 to about 4, comprising reacting a cyclic diamine of formula

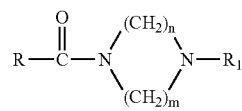

with a $C_3$–$C_4$ sultone, a halo-substituted $C_3$–$C_8$ cycloalkyl-, aryl-, $C_6$–$C_{10}$ arylalkyl-, $C_2$–$C_5$ hydroxyalkyl- or $C_1$–$C_5$ alkylsulfonate or a halo-substituted $C_3$–$C_8$ cycloalkyl-, aryl-, $C_6$–$C_{10}$ arylalkyl-, $C_2$–$C_5$ hydroxyalkyl- or $C_1$–$C_5$ alkylcarboxylate or carboxylic acid ester.

In another aspect, this invention is a tertiary amide of formula

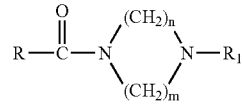

wherein R is selected from the group consisting of $C_{12}$–$C_{30}$ alkyl, $C_{12}$–$C_{30}$ alkenyl, $C_{12}$–$C_{30}$ arylalkyl and $C_{12}$–$C_{30}$ cycloalkylalkyl; $R_1$ is selected from cycloalkyl, aryl, $C_2$–$C_5$ hydroxyalkyl and $C_1$–$C_5$ alkyl; and m and n are independently integers of 1 to about 4.

In another aspect, this invention is a method of preparing a tertiary amide of formula

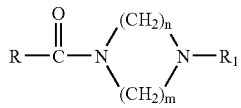

wherein R is selected from the group consisting of $C_{12}$–$C_{30}$ alkyl, $C_{12}$–$C_{30}$ alkenyl, $C_{12}$–$C_{30}$ arylalkyl and $C_{12}$–$C_{30}$ cycloalkylalkyl; $R_1$ is selected from $C_3$–$C_8$ cycloalkyl, aryl, $C_2$–$C_5$ hydroxyalkyl and $C_1$–$C_5$ alkyl; and m and n are independently integers of 1 to about 4 comprising reacting a carboxylic acid, ester or halide of formula

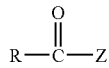

wherein Z is halide, alkoxy or hyroxy, with a cyclic diamine of formula

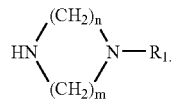

In a preferred aspect of this invention, the quaternized amido cyclic amine surfactant has formula (4) above where R is selected from the group consisting of $C_{12}-C_{30}$ alkyl and $C_{12}-C_{30}$ alkenyl.

In another aspect, this invention is a quaternized amido cyclic amine surfactant composition comprising about 40 to about 80 weight percent of the quaternized amidoamine surfactant prepared as described herein and about 20 to about 60 weight percent of one or more $C_1-C_4$ alcohols or $C_2-C_6$ diols.

After the quaternized amido cyclic amine surfactant in alcohol or diol composition is prepared, it may be necessary to dilute it with more alcohol, a diol and/or water if the product is a solid or not very pourable at room temperature. Isopropanol is the preferred alcohol and 1,2-propyleneglycol is the preferred diol for dilution. Surprisely, water drops the pour point.

Quaternized amido cyclic amine surfactants that contain a carbon—carbon double bond typically have lower melting points than the saturated counterpart. In some cases, this lower melting point allows for preparation of a composition that is liquid at room temperature.

Accordingly, in another preferred aspect, this invention is a quaternized amido cyclic amine surfactant having formula (4) above where R is $C_{12}-C_{30}$ alkenyl.

In another preferred aspect, R is $C_{18}-C_{30}$ alkenyl.

In another preferred aspect, m and n are both 2.

In another preferred aspect, $R_1$ is $C_1-C_2$ alkyl; $R_2$ is $C_1-C_2$ alkyl $C_6-C_8$ arylalkyl or $C_2-C_3$ hydroxyalkyl; and X is Cl.

In another preferred aspect, $R_1$ is methyl and $R_2$ is methyl, ethyl or hydroxyethyl.

In another preferred aspect, X is absent, $R_1$ is $C_1-C_5$ alkyl and $R_2$ is $C_1-C_5$ alkyl or $C_2-C_5$ hydroxyalkyl wherein the alkyl or hydroxyalkyl is substituted with carboxylate or sulfonate.

In another preferred aspect, $R_1$ is methyl and $R_2$ is —$CH_2CH_2CH_2SO_3$—.

The above compositions can be formulated with alcohols, glycols, water, inorganic or organic salts or an organic stabilizing additive to give a product that can be delivered to the field as a liquid. Alcohol solvents are preferably glycols and $C_1-C_8$ alcohols. Representative $C_1-C_8$ alcohols include methanol, isopropanol, n-propanol, butanol, 2-ethylhexanol, and the like, and mixtures thereof. Representative glycols include ethylene glycol, 1,2-propylene glycol, butylene glycol, 2-methyl-2,4-pentanediol, hexylene glycol, ethylene glycol butyl ether, and the like, and mixtures thereof. The alcohol and glycol also help solubilize the surfactant in water. Surprisingly, water helps drop the pour point of the above composition formulated in alcohols and glycols.

Accordingly, in another preferred aspect, this invention is a pourable aqueous composition comprising a) about 75 to about 90 weight percent of the quaternized amido cyclic amine surfactant solution in alcohol described above;

b) about 1 to about 15 weight percent of one or more glycols or $C_1-C_8$ alcohols; and c) about 1 to about 10 weight percent water.

In another preferred aspect, the $C_2-C_6$ diol is 1,2-propylene diol.

The solution of quaternized amido cyclic amine surfactant in water/alcohol in combination with one or more organic or inorganic salts or one or more $C_6-C_{10}$ alcohols is used to viscosify water or brine to form a gelled aqueous composition useful for treating a well drilled in a subterranean formation, for example for carrying proppants into subterranean formations during hydraulic fracturing of the formation. The gelled aqueous composition may also be used in detergent and cosmetic formulations and as a drift control agent in agricultural formulations.

Accordingly, in another aspect, this invention is a gelled aqueous composition comprising a) about 0.5 to about 10 weight percent of the quaternized amido cyclic amine surfactant in water/alcohol or diol described above;

b) about 0.5 to about 20 weight percent of one or more salts or one or more $C_6-C_{10}$ alcohols; and c) water.

The gelled aqueous solution is preferably prepared by adding the solution of quaternized amido cyclic amine surfactant in water/alcohol/diol to water and mixing or agitating. Then the salt, an aqueous solution of the salt or a $C_6-C_{10}$ alcohol is added to the surfactant/water/alcohol/diol solution in water and mixed or agitated.

Salts of ammonia and monovalent cations such as sodium and potassium are preferred. Preferred inorganic salts include ammonium chloride, potassium chloride and mixtures thereof. Preferred organic salts include alkali or alkaline-earth salts of salicylic acid, toluene sulphonate, 3-hydroxy-2-napthalenecarboxylate, cumene sulphonate, and the like. Preferably the alkali or alkaline earth metal is a monovalent cation such as sodium. A more preferred organic salt is sodium salicylate.

In general, a higher viscosity formulation is obtained when the hydrophobic portion of the quaternized amido cyclic amine surfactant consists of more than 15 carbons, preferably more than 18 carbons and more preferably at least 22 carbons up to about 30 carbons. Hydrophobic portion means the portion of the surfactant that contains only carbon atoms and no heteroatoms.

In a preferred aspect of this invention, the gelled aqueous composition is used in well treatment applications including drilling, hydraulic fracturing, gravel placement, scale removing and mud cake removing operations.

The gelled aqueous composition of this invention is particularly useful for carrying proppant into subterranean formations during hydraulic fracturing of the formation.

In hydraulic fracturing of subterranean formations, a fracturing fluid is injected through a wellbore penetrating the formation and is forced against the formation by pressure, forcing the formation strata or rock to crack and fracture. A particulate proppant is then placed in the fracture to prop open the fracture and provide improved flow of oil, gas or water into the wellbore.

Accordingly, in a preferred aspect, the gelled aqueous composition further contains one or more particulate proppants.

Suitable particulate proppant materials are insoluble in the fluids contained in the subterranean formation and include sand, bauxite, walnut shells, glass beads, polystyrene beads and the like.

In general, the gelled aqueous composition comprises about 0.5 pound to about 8 pound per gallon of the proppant, but may comprise up to 22 pounds or more of proppant in certain instances.

The fracturing fluid may contain other components conventional in the art including gases such as air, nitrogen or carbon dioxide to provide an energized fluid or a foam. Other conventional ingredients such as corrosion inhibitors, fluid-loss additives, and the like may also be included.

Other commonly used fracturing fluids are based on polysaccharides, such as guar. A disadvantage of the polysaccharide viscosifiers is that they contain materials that concentrate in the formation during the course of the hydraulic fracturing treatment, damaging the formation (reducing the porosity) and reducing the production of hydrocarbons after the fracturing event.

Quaternized amido cyclic amine surfactants form micelles that are able to viscosify the fluid and carry the proppant into the fractured rock. As oil is produced it breaks the micelle, allowing the components to be removed. Therefore, a breaker material may not be necessary, thereby reducing cost and improving clean-up of the fluid from the formation.

The foregoing may be better understood by reference to the following Examples, which are presented for purposes of illustration and are not intended to limit the scope of this invention.

EXAMPLE 1

1-Oleylamido-4-methylpiperazine

Methyl oleate (100.0 g, 0.3372 mole, Aldrich Chemical Company) and sodium methoxide (3.7 g) and 1-methypiperazine (37.2 g, 0.371 mole, Aldrich Chemical Company) are heated between 69° C. and 83° C. in a 4-neck 250 ml round bottom flask equipped with a condenser, Barrett trap, stirrer, thermocouple, heating assembly and nitrogen purge system for 1 hour, 26 minutes, during which time 3.7 milliliters of liquid is collected in the Barrett trap. The reaction mixture is then heated between 82° C. and 126° C. for an additional 10 hours, 35 minutes to give the title compound (120.1 g) as a yellow opaque viscous liquid. Infrared spectroscopy showes a sharp and large amide band at 1649 cm$^{-1}$.

EXAMPLE 2

4-Oleylamido(1-methyl)piperazonium propane sulfonate betaine

1-Oleylamido-4-methylpiperazine, (97.9 g, 0.27 moles), prepared as in Example 1, and water (203.4 g) are weighed into a 4-neck 500 ml round bottom flash equipped with a condenser, stirrer, thermocouple, heating assembly and nitrogen purge system. The contents are heated to 47° C. to give a viscous, beige and opaque liquid. Meanwhile, 1,3-propane sultone is warmed in an oven. A 50 ml addition funnel is attached to the round bottom flask and the melted 1,3-propane sultone (33.3 g, 0.27 moles) is added dropwise over 10 minutes. The reaction mixture is a yellow viscous liquid. The reaction mixture is heated between 73° C. and 75° C. for 50 minutes. Water (102.6 g) is added and the reaction mixture is heated between 66° C. and 79° C. for an additional 36 minutes. Isopropanol (29.9 g) is then added and the reaction mixture is heated between 76° C. and 79° C. for an additional 4 hours and 13 minutes. The reaction mixture is cooled to room temperature to give 430.4 g of a 28 weight percent 4-oleylamido(1-methyl)piperazonium propane sulfonate betaine, 6.40 weight percent isopropanol solution in water.

EXAMPLE 3

4.00 Weight Percent 4-oleylamido(1-methyl)piperazonium sulfonic betaine, 0.913 Weight Percent isopropanol, 6 Weight Percent KCl Solution in Water A portion (15.7 g) of the 28 weight percent 4-oleylamido (1-methyl)piperazonium propane sulfonate betaine, 6.40 weight percent isopropanol solution in water prepared in Example 2 is blended with water (81.4 g). Potassium chloride (6.6 g) is added and the contents are blended. Additional water (6.3 g) is added and contents are blended to give the title composition as a viscous solution.

EXAMPLE 4

3.99 Weight Percent 4-oleylamido(1-methyl)piperazonium sulfonate betaine, 0.913 Weight Percent isopropanol, 7.99 Weight Percent KCl Solution in Water A portion (15.7 g) of the 28 weight percent 4-oleylamido (1-methyl)piperazonium propane sulfonate betaine, 6.40 weight percent isopropanol solution in water prepared in Example 2 is blended with water (82.0 g). Potassium chloride (8.8 g) is added and the contents are blended. Additional water (3.6 g) is added and contents are blended to give the title composition as a viscous solution.

EXAMPLE 5

The compositions of Examples 3 and 4 are warmed in a oven at about 80° C. The viscosity is determined between 193° F. and 86° F. with a Brookfield Model DV-III Programmable Rheometer equipped with a SC4-34 spindle at a shear rate of 0.56 sec$^{-1}$. The results are shown in Table 1.

TABLE 1

Viscosity of Representative KCl Salt Compositions

| Temperature (° F.) | Example 3 6 wt. % KCl Viscosity (cps) | Temperature (° F.) | Example 4 7.99 wt. % KCl Viscosity (cps) |
|---|---|---|---|
| 193 | 495 | 193 | 150 |
| 185 | 540 | 186 | 180 |
| 176 | 675 | 175 | 210 |
| 167 | 825 | 168 | 240 |
| 159 | 975 | 158 | 330 |
| 149 | 1215 | 150 | 420 |
| 141 | 1515 | 141 | 630 |
| 132 | 2310 | 133 | 990 |
| 122 | 3374 | 122 | 1770 |
| 114 | 5654 | 114 | 2999 |
| 105 | 9748 | 104 | 5699 |
| 95 | 16496 | 95 | 10888 |
| 86 | 16496 | 86 | 23275 |

EXAMPLE 6

4.0 Weight Percent 4-oleylamido(1-methyl)piperazonium sulfonate betaine, 0.91 Weight Percent isopropanol, 10.0 Weight Percent KCl Solution in Water A portion (15.7 g) of the 28 weight percent 4-oleylamido (1-methyl)piperazonium propane sulfonate betaine, 6.40 weight percent isopropanol solution in water prepared in Example 2 is blended with water (82.2 g). Potassium chloride (11.0 g) is added and the contents are blended. Additional water (1.1 g) is added and contents are blended to give the title composition as a viscous solution in water.

EXAMPLE 7

4.0 Weight Percent 4-oleylamido(1-methyl)piperazonium sulfonate betaine, 0.91 Weight Percent isopropanol, 15.0 Weight Percent KCl Solution in Water A portion (15.7 g) of the 28 weight percent 4-oleylamido (1-methyl)piperazonium propane sulfonate betaine, 6.40 weight percent isopropanol solution in water prepared in Example 2 is blended with water (71.2 g). Potassium chloride (16.5 g) is added and the contents are blended. Additional water (6.6 g) is added and contents are blended to give the title composition as a viscous solution in water.

EXAMPLE 8

The compositions of Examples 6 and 7 are warmed in a oven at about 80° C. The viscosity is determined between 193° F. and 86° F. with a Brookfield Model DV-III Programmable Rheometer equipped with a SC4-34 spindle at a shear rate of 0.56 sec$^{-1}$. The results are shown in Table 2.

TABLE 2

Viscosity of Representative KCl Salt Compositions

| Temperature (° F.) | Example 6 10.0 wt. % KCl Viscosity (cps) | Temperature (° F.) | Example 7 15 wt. % KCl Viscosity (cps) |
|---|---|---|---|
| 193 | 180 | 193 | 120 |
| 186 | 180 | 186 | 90 |
| 175 | 180 | 177 | 90 |
| 167 | 240 | 167 | 90 |
| 158 | 300 | 157 | 90 |
| 148 | 390 | 150 | 90 |
| 139 | 600 | 141 | 90 |
| 130 | 870 | 132 | 90 |
| 122 | 1350 | 121 | 60 |
| 114 | 2130 | 113 | 90 |
| 104 | 3869 | 103 | 150 |
| 95 | 7558 | 96 | 480 |
| 87 | 16496 | 86 | 1230 |

EXAMPLE 9

4-Oleylamido-1-(2-hydroxyethyl)piperazine

Methyl oleate (100.0 g, 0.3372 mole, Aldrich Chemical Company), 25 weight percent sodium methoxide in methanol (3.7 g) and 1-(2-hydroxyethyl)piperazine (44.8 g, 0.344 mole, Aldrich Chemical Company) is heated at 72° C. to 83° C. in a 4-neck 250 ml round bottom flask equipped with a condenser, Barrett trap, stirrer, thermocouple, heating assembly and nitrogen purge system for 1 hour 13 minutes, during which time 4.0 ml of liquid collects in the Barrett trap. The reaction mixture is then heated at 83° C. to 131° C. for an additional 10 hours 58 minutes to give the title compound (129.8 g) as a light yellow opaque viscous liquid. Infrared spectrocopy shows a large amide band at 1642 cm$^{-1}$.

EXAMPLE 10

4-Oleylamido[1-(2-hydroxyethyl)piperazonium propane sulfonate betaine

4-Oleylamido[1-(2-hydroxyethyl)piperazonium propane sulfonate betaine (119.8 g, 0.327 moles), prepared as in Example 9, and water (240.8 g) are weighed into a 4-neck 500 ml round bottom flask equipped with a condenser, stirrer, thermocouple, heating assembly and nitrogen purge system and heated to 45° C. to give a viscous, beige and opaque liquid. Meanwhile, 1,3-propane sultone is warmed in an oven. A 50 ml addition funnel is attached to the round bottom flask and the warm 1,3-propane sultone (40.7 g, 0.333 moles) is added dropwise over 5 minutes. The reaction mixture is a yellow viscous liquid. The reaction mixture is heated at 70° C. to 84° C. for 1 hour, 49 minutes. Isopropanol (67.7 g) is then added and the reaction mixture is heated at 70° C. to 72° C. for an additional 4 hours and 35 minutes. The reaction mixture (448.0 g) is cooled to room temperature to give a 35.8 weight percent 4-oleylamido[1-(2-hydroxyethyl)piperazonium propane sulfonate betaine, 15.11 weight percent isopropanol solution in water.

EXAMPLE 11

4.0 Weight Percent 4-oleylamido[1-(2-hydroxyethyl)piperazonium propane sulfonate betaine, 1.69 Weight Percent isopropanol, 1 Weight Percent KCl Solution in Water A portion (12.3 g) of the 35.8 weight percent 4-oleylamido[1-(2-hydroxyethyl)piperazonium propane sulfonate betaine, 15.11 weight percent isopropanol solution in water from Example 10 is blended with water (81.5 g). Potassium chloride (1.1 g) is added and the contents are blended. Additional water (15.2 g) is added and the contents are blended to give the title composition as a viscous solution in water.

EXAMPLE 12

5.97 Weight Percent 4-oleylamido[1-(2-hydroxyethyl)piperazonium propane sulfonate betaine, 2.52 Weight Percent isopropanol, 1 Weight Percent KCl Solution in Water A portion (18.4 g) of the 35.8 weight percent 4-oleylamido[1-(2-hydroxyethyl)piperazonium propane sulfonate betaine, 15.11 weight percent isopropanol solution in water from Example 10 is blended with water (90.9 g). Potassium chloride (1.1 g) is added and the contents are blended to give the title composition as a viscous solution in water.

EXAMPLE 13

6.98 Weight Percent 4-oleylamido[1-(2-hydroxyethyl)piperazonium propane sulfonate betaine, 2.94 Weight Percent isopropanol, 1 Weight Percent KCl Solution in Water A portion (21.5 g) of the 35.8 weight percent 4-oleylamido[1-(2-hydroxyethyl)piperazonium propane sulfonate betaine, 15.11 weight percent isopropanol solution in water from Example 10 is blended with water (82.9 g). Potassium chloride (1.1 g) is added and the contents are blended. Additional water (4.7 g) is added and the contents are blended to give the title composition as a viscous solution in water.

EXAMPLE 14

The compositions of Examples 11, 12 and 13 are warmed in a oven at about 80° C. The viscosity is determined between 193° F. and 86° F. with a Brookfield Model DV-III Programmable Rheometer equipped with a SC4-34 spindle at a shear rate of 0.56 sec$^{-1}$. The results are shown in Table 3.

EXAMPLE 15

4-Erucylamido-1,1-dimethylpiperazonium chloride

Erucic acid (810 g, Iodine value 74–78) and 1-methylpiperazine (242 g) are heated in a 2-liter high pressure vessel at a temperature up to 160° C. for 24 hours to give 4-erucylamido(1-methyl)piperazine.

The 4-Erucylamido(1-methyl)piperazine (630 g), methyl chloride (81 g) and isopropanol (237 g) are heated in a 2-liter pressure vessel at a temperature up to 100° C. for 19 hours. A chloride titration indicates the resulting material is 69.7% active in isopropanol. The product is a cream colored opaque paste at room temperature.

EXAMPLE 16

3.96 Weight Percent 4-erucylamido-1,1-dimethylpiperazonium chloride, 1.72 Weight Percent isopropanol, 2.71 Weight Percent ammonium chloride Solution in Water A portion (6.3 g) of the 69.7 weight percent 4-erucylamido-1,1-dimethylpiperazonium chloride, in 30.3 weight percent isopropanol composition from Example 15 is blended with water (80.0 g). Ammonium chloride (3.0 g) is added and the contents are blended. Additional water (21.5 g) is added and contents are blended to give the title composition as a viscous solution in water.

EXAMPLE 17

3.99 Weight percent 4-erucylamido-1,1-dimethylpiperazonium chloride, 1.74 weight percent isopropanol, 3.00 weight KCl solution in water.

A portion (6.3 g) of the 69.7 wt. % 4-erucylamido-1,1-dimethylpiperazonium chloride, 30.3 weight percent isopropanol composition of Example 15 is blended with water (82.4 g). Potassium chloride (3.3 g) is added and the contents are blended. Additional water (18.0 g) is added and the contents are blended to give the title composition as a viscous solution in water.

EXAMPLE 18 (COMPARATIVE EXAMPLE)

4.02 Weight Percent bis(2-hydroxyethyl)-13-docosen-1-amine methyl chloride quaternary, 1.34 Weight Percent isopropanol, 4.0 Weight Percent KCl Solution in Water Bis(2-hydroxyethyl)-13-docosen-1-amine methyl chloride quaternary salt (5.9 g, 75 weight percent solution in isopropanol) is blended with water (91.3 g). Bis(2-hydroxyethyl)-13-docosen-1-amine is available from Akzo Nobel as Ethoquad E/12-75. Potassium chloride (4.4 g) is added and

TABLE 3

Viscosity of Representative KCl Salt Compositions

| Temperature (° F.) | Example 11 4 wt. % Amide Quat. Viscosity (cps) | Temperature (° F.) | Example 12 5.97 wt. % Amide Quat. Viscosity (cps) | Temperature (° F.) | Example 13 6.98 wt. % Amide Quat. Viscosity (cps) |
|---|---|---|---|---|---|
| 193 | 60 | 193 | 180 | 193 | 60 |
| 185 | 60 | 184 | 150 | 186 | 60 |
| 177 | 60 | 177 | 90 | 175 | 90 |
| 169 | 60 | 167 | 90 | 167 | 60 |
| 159 | 30 | 158 | 30 | 158 | 60 |
| 150 | 30 | 149 | 60 | 148 | 60 |
| 141 | 60 | 140 | 60 | 139 | 90 |
| 132 | 90 | 131 | 90 | 130 | 90 |
| 121 | 270 | 122 | 120 | 122 | 120 |
| 113 | 810 | 112 | 270 | 113 | 210 |
| 103 | 2220 | 104 | 780 | 104 | 360 |
| 96 | 3809 | 95 | 2879 | 94 | 870 |
| 86 | 4919 | 86 | 16616 | 86 | 4289 | the contents are mixed. Additional water (7.4 g) is added and the contents are mixed to give the title composition as a viscous solution in water.

EXAMPLE 19

The viscosity of the compositons of Examples 16 and 17 is measured between 71° F. and 260° F. and the viscosity of Comparative Example 18 is measured between 81° F. and 275° F. with a Fann 50 Rheometer equipped with a R1-B5 spindle setting at a shear rate of 118 RPM. The results are shown in Table 4.

TABLE 4

Viscosity of Representative $NH_4Cl$ and KCl Salt Compositions

| Temperature (° F.) | Example 16 2.71 wt. % $NH_4Cl$ Viscosity (cps) | Temperature (° F.) | Example 17 3.0 wt. % KCl Viscosity (cps) | Temperature (° F.) | Comp. Ex. 18 4 wt. % KCl Viscosity (cps) |
|---|---|---|---|---|---|
| 257 | 22 | 252 | 19 | 242 | 23 |
| 252 | 32 | 246 | 26 | 233 | 27 |
| 244 | 52 | 239 | 41 | 226 | 30 |
| 237 | 83 | 229 | 87 | 219 | 38 |
| 230 | 153 | 214 | 191 | 209 | 59 |
| 212 | 241 | 165 | 161 | 202 | 91 |
| 163 | 126 | 100 | 54 | 193 | 156 |
| 97 | 52 | 74 | 189 | 183 | 262 |
| 77 | 147 | | | 174 | 341 |
| | | | | 165 | 376 |
| | | | | 157 | 401 |
| | | | | 147 | 505 |
| | | | | 138 | 615 |
| | | | | 128 | 691 |
| | | | | 116 | 721 |
| | | | | 103 | 636 |
| | | | | 90 | 606 |
| | | | | 81 | 602 |

100 cps at a shear rate of 100 $sec^{-1}$ is preferred to fracture a formation. Table 4 shows that the material of Example 16 and 17 provides more than 100 cps of viscosity at 233° F. and 226° F., respectively, while the material of Comparative Example 18 provides more than 100 cps of viscosity at 193° F. Therefore, the material of Examples 16 and 17 can be used to fracture hotter wells than the material of Example 18.

EXAMPLE 20

4-Erucylamido-1-methyl-1-(2-hydroxyethyl)piperazonium chloride

Erucic acid (851 g, 2.51 moles, Iodine value 60–70) and 1-(2-hydroxyethyl)piperazine (327 g, 2.51 moles) are heated in a 2-liter pressure vessel at a temperature up to 161° C. for 28 hours to prepare 4-erucylamido-1-(2-hydroxyethyl)piperazine.

The 4-Erucylamido-1-(2-hydroxyethyl)piperazine (687 g), methyl chloride (96 g) and isopropanol (261 g) are heated at a temperature up to 100° C. for 6 hours in a 2-liter pressure vessel. A chloride titration indicates that the resulting cream colored paste is 66.4% active in isopropanol.

EXAMPLE 21

5.97 Weight Percent 4-erucylamido-1-methyl-1-(2-hydroxyethyl)piperazonium chloride, 3.02 Weight Percent isopropanol, 0.99 Weight Percent potassium chloride Solution in Water A portion (9.9 g) of the 66.4 weight percent 4-erucylamido-1-methyl-1-(2-hydroxyethyl)piperazonium chloride composition of Example 20 is blended with water (86.3 g). Potassium chloride (1.1 g) is added and the contents are blended. Additional water (12.8 g) is added and contents are blended to give the title composition as a viscous solution in water.

EXAMPLE 22

7.06 Weight Percent 4-erucylamido-1-methyl-1-(2-hydroxyethyl)piperazonium chloride, 3.57 Weight Percent isopropanol, 1.00 Weight Percent potassium chloride Solution in Water A portion (11.7 g) of the 66.4 weight percent 4-erucylamido-1-methyl-1-(2-hydroxyethyl)piperazonium chloride composition of Example 20 is blended with water (81.1 g). Potassium chloride (1.1 g) is added and the contents are blended. Additional water (16.2 g) is added and contents are blended to give the title composition as a viscous solution in water.

EXAMPLE 23

The compositions of Examples 21 and 22 are warmed in an oven at about 80° C. The viscosity is determined between 193° F. and 86° F. with a Brookfield Model DV-III Programmable Rheometer equipped with a SC4-34 spindle at a shear rate of 0.56 $sec^{-1}$. The results are shown in Table 5.

TABLE 5

Viscosity of Representative KCl Salt Compositions

| Temperature (° F.) | Example 21 5.97% Quat 1% KCl Viscosity (cps) | Temperature (° F.) | Example 22 7.06% Quat. 1% KCl Viscosity (cps) |
|---|---|---|---|
| 193 | 1200 | 193 | 1140 |
| 184 | 1890 | 186 | 1500 |
| 176 | 4469 | 176 | 3929 |
| 167 | 11248 | 169 | 7528 |
| 159 | 17576 | 158 | 16946 |
| 149 | 15897 | 149 | 23485 |
| 140 | 14097 | 141 | 19706 |
| 132 | 13137 | 131 | 17216 |
| 124 | 11967 | 120 | 14547 |
| 115 | 9988 | 115 | 13617 |
| 106 | 8368 | 105 | 11398 |
| 100 | 6899 | 99 | 9778 |
| 95 | 5699 | 95 | 8278 |
| 90 | 4259 | 89 | 6359 |
| 86 | 3509 | 86 | 4529 |

EXAMPLE 24

1,1-Dimethylpiperazino-4-oleylamide ammonium chloride

Oleic acid (822 g, 2.91 moles, Iodine value 199–204) and 1-methylpiperazine (295 g, 2.94 moles) are heated in a 2-liter pressure vessel at a temperature up to 120° C. for 22 hours to provide 1-methylpiperazino-4-oleamide.

The 1-methylpiperazino-4-oleamide (634 g), methyl chloride (93 g) and isopropanol (242 g) are heated at a temperature up to 100° C. for 8 hours in a 2-liter pressure vessel. A chloride titration indicates that the resulting amber colored liquid is 75.1% active in isopropanol.

EXAMPLE 25

4.03 Weight Percent 1,1-dimethylpiperazino-4-oleylamide ammonium chloride, 1.34 Weight Percent isopropanol, 4.0 Weight Percent potassium chloride Solution in Water A portion (5.9 g) of the 75.1 weight percent 1,1-dimethylpiperazino-4-oleylamide ammonium chloride solution in isopropanol of Example 24 is blended with water (80.2 g). Potassium chloride (4.4 g) is added and the contents are blended. Additional water (19.5 g) is added and the contents are blended to give the title composition as a viscous solution in water.

EXAMPLE 26

The composition of Example 25 is warmed in an oven at about 80° C. The viscosity is determined between 193° F. and 86° F. with a Brookfield Model DV-III Programmable Rheometer equipped with a SC4-34 spindle at a shear rate of 0.56 sec$^{-1}$. The results are shown in Table 6.

TABLE 6

Viscosity of a Representative KCl Salt Composition

| Temperature (° F.) | Example 25 4.03% Quat 4.0% KCl Viscosity (cps) |
|---|---|
| 193 | 660 |
| 190 | 660 |
| 186 | 720 |
| 179 | 840 |
| 175 | 1020 |
| 170 | 1440 |
| 166 | 1950 |
| 160 | 3149 |
| 155 | 5189 |
| 151 | 7258 |
| 146 | 11757 |
| 140 | 17876 |
| 135 | 15297 |
| 130 | 15657 |
| 125 | 14907 |
| 120 | 14367 |
| 115 | 14037 |
| 111 | 13587 |
| 105 | 13197 |
| 100 | 13467 |
| 96 | 13977 |
| 90 | 14457 |
| 86 | 11817 |

As shown in Table 4, representative unsaturated quaternized amido cyclic amine surfactants maintain more than 100 cps viscosity at a higher temperature (226° F.) than the comparative composition of Example 18 (200° F.) when formulated with KCl. The unsaturated amido alkylpiperazine quaternary surfactant maintains more than 100 cps viscosity at an even higher temperature (233° F.) when formulated with NH$_4$Cl. Therefore, use of the quaternized amido cyclic amine surfactant of this invention permit fracturing of wells at hotter temperatures than current treatments.

Although this invention has been described in detail for the purpose of illustration, it is to be understood that such detail is solely for that purpose and that numerous modifications, alterations and changes can be made therein by those skilled in the art without departing from the spirit and scope of the invention except as it may be limited by the claims. All changes which come within the meaning and range of equivalency of the claims are to be embraced within their scope.

The invention claimed is:

1. A quaternized amido cyclic amine surfactant of formula

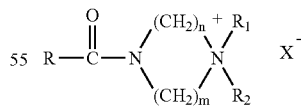

wherein R is selected from the group consisting of C$_{12}$–C$_{30}$ alkenyl, C$_{12}$–C$_{30}$ arylalkyl and C$_{12}$–C$_{30}$ cycloalkylalkyl; R$_1$ and R$_2$ are independently selected from C$_3$–C$_8$ cycloalkyl, aryl, C$_6$–C$_{10}$ arylalkyl, C$_2$–C$_5$ hydroxyalkyl and C$_1$–C$_5$ alkyl; m and n are independently integers of 1 to about 4; X is absent; and one of R$_1$ and R$_2$ is substituted with carboxylate or sulfonate.

2. The quaternized amido cyclic amine surfactant of claim 1 wherein R is C$_{12}$–C$_{30}$ alkenyl.

3. The quaternized amido cyclic amine surfactant of claim 2 wherein R is $C_{18}$–$C_{30}$ alkenyl.

4. The quaternized amido cyclic amine surfactant of claim 3 wherein m and n are both 2.

5. The quaternized cyclic diamine of claim 4 wherein $R_1$ is $C_1$–$C_5$ alkyl and $R_2$ is $C_1$–$C_5$ alkyl or $C_2$–$C_5$ hydroxyalkyl wherein the alkyl or hydroxyalkyl is substituted with carboxylate or sulfonate.

6. The quaternized cyclic diamine of claim 5 wherein $R_1$ is methyl and $R_2$ is —$CH_2CH_2CH_2SO_3^-$.

7. An aqueous composition comprising
  a) about 75 to about 90 weight percent of a quaternized cyclic diamine composition comprising about 20 to about 60 weight percent of one or more $C_1$–$C_4$ alcohols or $C_2$–$C_6$ diols and about 40 to about 80 weight percent of one or more quaternized cyclic diamines of formula

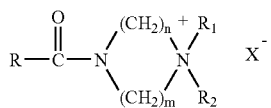

wherein R is selected from the group consisting of $C_{12}$–$C_{30}$ alkyl, $C_{12}$–$C_{30}$ alkenyl, $C_{12}$–$C_{30}$ arylalkyl and $C_{12}$–$C_{30}$ cycloalkylalkyl; $R_1$ and $R_2$ are independently selected from $C_3$–$C_8$ cycloalkyl, aryl, $C_6$–$C_{10}$ arylalkyl, $C_2$–$C_5$ hydroxyalkyl and $C_1$–$C_5$ alkyl; m and n are independently integers of 1 to about 4; and X is absent or is selected from halide and methyl sulfate, provided that when X is absent, one of $R_1$ and $R_2$ is substituted with carboxylate or sulfonate;
  b) about 1 to about 15 weight percent of one or more glycols or $C_1$–$C_8$ alcohols; and
  c) about 1 to about 10 weight percent water.

8. The aqueous composition of claim 7 wherein the $C_1$–$C_4$ alcohol is isopropanol.

9. The aqueous composition of claim 7 wherein the $C_2$–$C_6$ diol is 1,2-propane diol.

10. A gelled aqueous composition comprising
  a) about 0.5 to about 10 weight percent of the aqueous composition of claim 7;
  b) about 0.5 to about 20 weight percent of one or more salts or one or more $C_4$–$C_{10}$ alcohols; and
  c) water.

11. The gelled aqueous composition of claim 10 wherein the salt is potassium chloride, ammonium chloride or sodium salicylate.

12. The gelled aqueous composition of claim 10 wherein the $C_4$–$C_{10}$ alcohol is selected from the group consisting of hexanol, octanol and decanol.

13. The gelled aqueous composition of claim 10 further comprising one or more particulate proppants suspended therein.

14. A method of preparing a quaternized cyclic diamine of formula

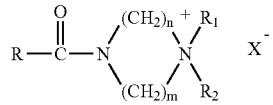

wherein R is selected from the group consisting of $C_{12}$–$C_{30}$ alkyl, $C_{12}$–$C_{30}$ alkenyl, $C_{12}$–$C_{30}$ arylalkyl and $C_{12}$–$C_{30}$ cycloalkylalkyl; $R_1$ is selected from $C_3$–$C_8$ cycloalkyl, aryl, $C_6$–$C_{10}$ arylalkyl, $C_2$–$C_5$ hydroxyalkyl and $C_1$–$C_5$ alkyl; $R_2$ is selected from $C_3$–$C_8$ cycloalkyl, aryl, $C_6$–$C_{10}$ arylalkyl, $C_2$–$C_5$ hydroxyalkyl and $C_1$–$C_5$ alkyl wherein the cycloalkyl, aryl, arylalkyl, hydroxyalkyl or alkyl is substituted with carboxylate or sulfonate; m and n are independently integers of 1 to about 4; and X absent, comprising reacting a cyclic diamine of formula

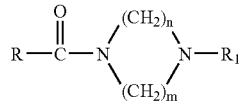

with a $C_3$–$C_4$ sultone, a halo-substituted $C_3$–$C_8$ cycloalkyl-, aryl-, $C_6$–$C_{10}$ arylalkyl-, $C_2$–$C_5$ hydroxyalkyl- or $C_1$–$C_5$ alkylsulfonate or a halo-substituted $C_3$–$C_8$ cycloalkyl-, aryl-, $C_6$–$C_{10}$ arylalkyl-, $C_2$–$C_5$ hydroxyalkyl- or $C_1$–$C_5$ alkylcarboxylate or carboxylic acid ester.

15. The method of claim 14 wherein the cyclic diamine is reacted with 1,3-propane sultone, sodium salt of 3-chloro-2-hydroxy-1-propanesulfonic acid or sodium chloroacetate.

16. The aqueous composition of claim 7 wherein R is selected from the group consisting of $C_{12}$–$C_{30}$ alkyl and $C_{12}$–$C_{30}$ alkenyl.

17. The aqueous composition of claim 16 wherein R is $C_{12}$–$C_{30}$ alkenyl.

18. The aqueous composition of claim 16 wherein R is $C_{18}$–$C_{30}$ alkenyl.

19. The aqueous composition of claim 18 wherein m and n are both 2.

20. The aqueous composition of claim 19 wherein $R_1$ is $C_1$–$C_2$ alkyl; and $R_2$ is $C_1$–$C_2$ alkyl, $C_6$–$C_8$ arylalkyl or $C_2$–$C_3$ hydroxyalkyl.

21. The aqueous composition of claim 20 wherein $R_1$ is methyl and $R_2$ is methyl, ethyl or hydroxyethyl.

22. The aqueous composition of claim 21 wherein $R_1$ and $R_2$ are methyl.

\* \* \* \* \*